US00PP28301P2

(12) United States Plant Patent
Koning

(10) Patent No.: US PP28,301 P2
(45) Date of Patent: Aug. 15, 2017

(54) ***LAVANDULA* PLANT NAMED 'ANOUK DELUXE 1173'**

(50) Latin Name: *Lavandula stoechas*
Varietal Denomination: Anouk Deluxe 1173

(71) Applicant: Lammert Koning, Nuis (NL)

(72) Inventor: Lammert Koning, Nuis (NL)

(73) Assignee: L. Koning Beheer B.V., Nuis (NL)

( * ) Notice: Subject to any disclaimer, the term of this patent is extended or adjusted under 35 U.S.C. 154(b) by 0 days.

(21) Appl. No.: 14/999,139

(22) Filed: Mar. 31, 2016

(51) Int. Cl.
*A01H 5/02* (2006.01)

(52) U.S. Cl.
USPC ..... Plt./445

(58) Field of Classification Search
USPC ..... Plt./445
See application file for complete search history.

*Primary Examiner* — Annette Para
(74) *Attorney, Agent, or Firm* — C. A. Whealy

(57) ABSTRACT

A new and distinct cultivar of *Lavandula* plant named 'Anouk Deluxe 1173', characterized by its compact and broadly upright plant habit; freely branching growth habit; freely flowering habit; dark violet blue-colored flowers with numerous white-colored terminal flower bracts positioned on strong and erect peduncles; terminal flower bracts are tolerant to full sunlight conditions; long flowering period; and good garden performance.

2 Drawing Sheets

Botanical designation: *Lavandula stoechas.*
Cultivar denomination: 'ANOUK DELUXE 1173'.

BACKGROUND OF THE INVENTION

The present invention relates to a new and distinct *Lavandula* plant, botanically known as *Lavandula stoechas*, commonly referred to as Lavender and hereinafter referred to by the name 'Anouk Deluxe 1173'.

The new *Lavandula* plant is a product of a planned breeding program conducted by the Inventor in Boskoop, The Netherlands. The objective of the breeding program was to develop new unique *Lavandula* plants with good performance and attractive plant form and flower coloration.

The new *Lavandula* plant originated from a cross-pollination made by the Inventor in May, 2010 of a proprietary selection of *Lavandula stoechas* identified as code number 1115, not patented, as the female, or seed, parent with a proprietary selection of *Lavandula stoechas* identified as code number L.91, not patented, as the male, or pollen, parent. The new *Lavandula* plant was discovered and selected by the Inventor as a single flowering plant within the progeny of the stated cross-pollination in a controlled environment in Boskoop, The Netherlands in May, 2011.

Asexual reproduction of the new *Lavandula* plant by terminal cuttings in a controlled greenhouse environment in Boskoop, The Netherlands since August, 2011 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Anouk Deluxe 1173' as a new and distinct *Lavandula* plant:

1. Compact and broadly upright plant habit.
2. Freely branching growth habit.
3. Freely flowering habit.
4. Dark violet blue-colored flowers with numerous white-colored terminal flower bracts positioned on strong and erect peduncles; terminal flower bracts are tolerant to full sunlight conditions.
5. Long flowering period.
6. Good garden performance.

Plants of the new *Lavandula* differ primarily from plants of the female parent selection in garden performance as plants of the new *Lavandula* are more tolerant to full sunlight conditions than terminal flower bracts of plants of the female parent selection.

Plants of the new *Lavandula* differ primarily from plants of the male parent selection in growth development as plants of the new *Lavandula* are more herbaceous and less woody than plants of the male parent selection.

Plants of the new *Lavandula* can be compared to plants of the *Lavandula stoechas* 'Madrid White', not patented. In side-by-side comparisons, plants of the new *Lavandula* differ primarily from plants of 'Madrid White' in the following characteristics:

1. Plants of the new *Lavandula* have longer terminal flower bracts than plants of 'Madrid White'.
2. Terminal flower bracts of plants of the new *Lavandula* are more tolerant to full sunlight conditions than terminal flower bracts of plants of 'Madrid White'.

Plants of the new *Lavandula* can be compared to plants of the *Lavandula stoechas* 'White Summer', not patented. In side-by-side comparisons, plants of the new *Lavandula* differ primarily from plants of 'White Summer' in the following characteristics:

1. Plants of the new *Lavandula* have longer terminal flower bracts than plants of 'White Summer'.
2. Terminal flower bracts of plants of the new *Lavandula* are brighter white in color and are more tolerant to full sunlight conditions than terminal flower bracts of plants of 'White Summer'.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet is a side perspective view of a typical flowering plant of 'Anouk Deluxe 1173' grown in a container.

The photograph on the second sheet is a close-up view of a typical flowering plant of 'Anouk Deluxe 1173'.

DETAILED BOTANICAL DESCRIPTION

Plants used in the aforementioned photographs and following detailed description were grown in 15-cm containers during the spring and early summer in an outdoor nursery in Boskoop, The Netherlands and under cultural practices typical of commercial *Lavandula* production. Plants were ten months old when the photographs and description were taken. During the production of the plants, day temperatures ranged from 10° C. to 22° C. and night temperatures ranged from 2° C. to 12° C. In the following description, color references are made to The Royal Horticultural Society Colour Chart, 2007 Edition, except where general terms of ordinary dictionary significance are used.

Botanical classification: *Lavandula stoechas* 'Anouk Deluxe 1173'.

Parentage:

*Female, or seed, parent*.—Proprietary selection of *Lavandula stoechas* identified as code number 1115, not patented.

*Male, or pollen, parent*.—Proprietary selection of *Lavandula stoechas* identified as code number L.91, not patented.

Propagation:

*Type*.—Terminal vegetative cuttings.

*Time to initiate roots, summer and winter*.—About ten days at temperatures about 18° C.

*Time to produce a rooted young plant, summer*.—About 60 days at temperatures about 20° C.

*Time to produce a rooted young plant, winter*.—About 70 days at temperatures about 20° C.

*Root description*.—Fine, fibrous; initially white in color and becoming more brown with development; actual color of the roots is dependent on substrate composition, water quality, fertilizer type and formulation.

*Rooting habit*.—Freely branching; dense.

Plant description:

*Plant and growth habit*.—Herbaceous perennial; compact and broadly upright plant habit; freely branching habit; moderately vigorous growth habit; flowers arranged in verticillasters on crowded spikes with showy terminal flower bracts.

*Plant height, soil level to top of floral plane*.—About 20 cm.

*Plant width*.—About 39.3 cm.

*Lateral branch description*.—Quantity per plant: About 54 primary lateral branches developing per plant with numerous secondary branches. Length: About 10.8 cm. Diameter: About 3 mm. Internode length: About 1.8 cm. Strength: Strong. Aspect: Upright to outwardly. Texture and luster: Densely tomentose; matte. Color: Close to 144B; pubescence, close to 157D.

*Leaf description*.—Arrangement: Opposite, simple; sessile. Length: About 4.5 cm. Width: About 1 cm. Shape: Narrowly oblanceolate. Apex: Acute. Base: Cuneate. Margin: Entire; revolute. Texture and luster, upper and lower surfaces: Moderately tomentose; matte. Fragrance: Strongly aromatic, pungent. Venation pattern: Pinnate. Color: Developing leaves, upper surface: Close to 143A. Developing leaves, lower surface: Close to 143B. Fully expanded leaves, upper surface: Close to N137C; venation, close to 144B to 144C; pubescence, close to 157B. Fully expanded leaves, lower surface: Close to 137B to 137C; venation, close to 147C; pubescence, close to 157B.

Flower description:

*Flower type, arrangement and habit*.—Small single salverform flowers arranged in compact verticillasters on crowded terminal spikes; freely flowering, about 160 flowers developing per inflorescence and more than 8,500 flowers developing per plant; flowers with two-lobed upper lip and three-lobed lower lip; flowers face mostly outwardly on the spike; inflorescences with numerous showy terminal flower bracts.

*Natural flowering season*.—Long flowering period; continuous from late spring into late summer in The Netherlands.

*Flower longevity on the plant*.—Individual flowers last about ten days on the plant; flowers not persistent.

*Fragrance*.—None detected.

*Flower buds*.—Length: About 4 mm. Diameter: About 1 mm. Shape: Oblong. Texture and luster: Moderately tomentose; matte. Color: Close to 137B; towards the base, close to 145B to 145C.

*Inflorescence size*.—Height: About 5.5 cm. Diameter, at terminal flower bracts: About 3.8 cm. Diameter, below flower bracts: About 1.5 cm.

*Flower size*.—Diameter: About 5 mm. Depth (height): About 8 mm.

*Petals*.—Quantity and arrangement: Upper lip, two-lobed and lower lip, three-lobed. Length, upper lip: About 8 mm. Length, lower lip: About 7 mm. Width, upper lip: About 4 mm. Width, lower lip: About 5 mm. Shape: Roughly spatulate; lower 62.5% fused into a tube. Apex: Obtuse, rounded. Margin: Entire. Texture and luster, upper (inner) and lower (outer) surfaces: Smooth, glabrous; matte. Color: When opening and fully opened, upper (inner) surface: Close to N92D; throat, close to 84A, towards the base, close to N155D; color does not fade with development. When opening and fully opened, lower (outer) surface: Close to N92D; tube, close to 84A, towards the base, close to N155D; color does not fade with development.

*Terminal flower bracts*.—Quantity and arrangement: Numerous, about seven to twelve positioned upright at inflorescence apex. Length: About 2.2 cm. Width: About 1.1 cm. Shape: Oblong. Apex: Broadly acute. Base: Cuneate. Margin: Entire; undulate. Texture and luster, upper and lower surfaces: Smooth, glabrous; matte. Color, upper and lower surfaces: Close to between NN155B and 157D; venation, close to 143A to 143B.

*Basal flower bracts*.—Quantity and arrangement: Each group of seven flowers is subtended by a single basal flower bract. Length: About 8 mm. Width: About 1 cm. Shape: Broadly rhomboidal. Apex: Aristate. Base: Cuneate. Margin: Entire. Texture and luster, upper and lower surfaces: Moderately tomentose; matte. Color, upper and lower surfaces: Close to 157B to 157D; venation, close to 143A to 143B; pubescence, close to NN155D.

*Sepals*.—Quantity and arrangement: Five, fused into a campanulate tube. Length: About 4 mm. Width: About 1.5 mm. Shape: Lanceolate. Apex: Acute. Margin: Entire. Texture and luster, upper (inner) and lower (outer) surfaces: Densely pubescent; matte. Color: When opening, upper (inner) and lower (outer) surfaces: Close to 143A; towards the base, close to 145B to 145C; pubescence, close to NN155C to NN155D. Fully opened, upper (inner) and lower (outer) surfaces: Close to 143A; towards the base, close to 145C; pubescence, close to NN155C to NN155D.

*Peduncles*.—Length: About 8.3 cm. Diameter: About 3 mm. Aspect: Mostly upright. Strength: Strong. Texture and luster: Densely tomentose; matte. Color: Close to 144B; pubescence, close to 157D.

*Reproductive organs*.—Stamens: Quantity per flower: Four. Filament length: About 2 mm. Anther shape: Reniform. Anther length: About 1 mm. Anther color: Close to 13B. Pollen amount: Moderate. Pollen color: Close to 17B. Pistils: Quantity per flower: One. Pistil length: About 2 mm. Stigma shape: Club-shaped. Stigma color: Close to 141B. Style length: About 1.5 mm. Style color: Close to 157B to 157D. Ovary color: Close to 143B.

*Seeds and fruits*.—Seed and fruit production has not been observed on plants of the new *Lavandula*.

Disease & pest resistance: Plants of the new *Lavandula* have not been noted to be resistant to pathogens and pests common to *Lavandula* plants.

Garden performance: Plants of the new *Lavandula* have exhibited good tolerance to rain and wind and have been observed to tolerate high temperatures about 40° C. and to be hardy to USDA Hardiness Zone 7. Terminal flower bracts are tolerant to full sunlight conditions and typically do not sun scald or scorch.

It is claimed:

1. A new and distinct *Lavandula* plant named 'Anouk Deluxe 1173' as illustrated and described.

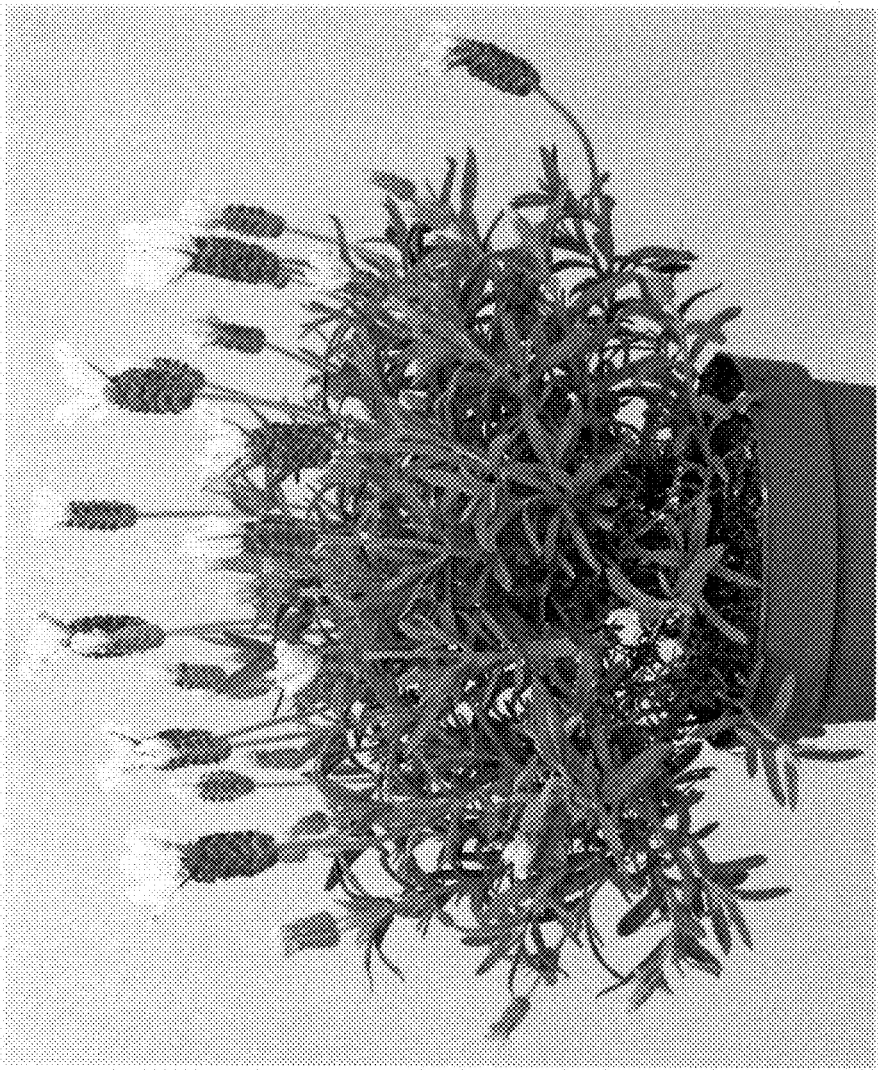

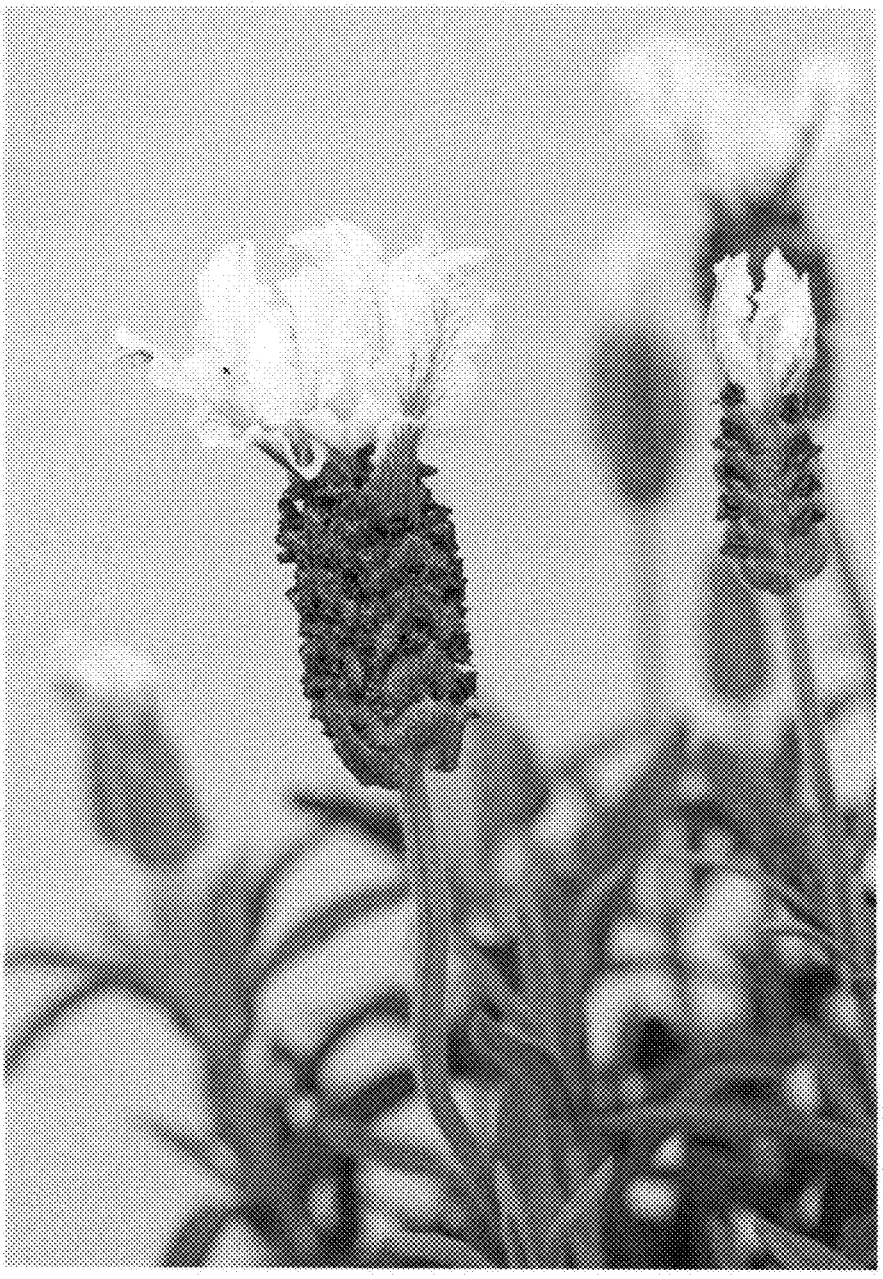

* * * * *